(12) United States Patent
Kikuchi et al.

(10) Patent No.: US 7,158,609 B2
(45) Date of Patent: Jan. 2, 2007

(54) X-RAY CRYSTAL ORIENTATION MEASURING METHOD AND X-RAY CRYSTAL ORIENTATION MEASURING APPARATUS

(75) Inventors: Tetsuo Kikuchi, Tachikawa (JP); Yoshio Inago, Ome (JP); Makoto Usui, Musashimurayama (JP); Toshio Uematsu, Tachikawa (JP)

(73) Assignee: Rigaku Corporation, Tokyo (JP)

( * ) Notice: Subject to any disclaimer, the term of this patent is extended or adjusted under 35 U.S.C. 154(b) by 148 days.

(21) Appl. No.: 10/939,471

(22) Filed: Sep. 14, 2004

(65) Prior Publication Data

US 2005/0078790 A1 Apr. 14, 2005

(30) Foreign Application Priority Data

Oct. 14, 2003 (JP) ............................. 2003-353278

(51) Int. Cl.
*G01N 23/207* (2006.01)
(52) U.S. Cl. .............................. 378/73; 378/70; 378/71
(58) Field of Classification Search ............ 378/70–73
See application file for complete search history.

(56) References Cited

U.S. PATENT DOCUMENTS 5,588,034 A 12/1996 Bowen et al. ................ 378/73
7,001,462 B1 * 2/2006 Genier et al. ............... 117/201

FOREIGN PATENT DOCUMENTS

| DE | 3236109 | 4/1983 |
|---|---|---|
| GB | 2107560 | 4/1983 |
| JP | 57-136150 | 8/1982 |
| JP | 57-136151 | 8/1982 |
| JP | 3-058058 | 9/1991 |
| JP | 4-059581 | 9/1992 |
| JP | 2001-13092 | 1/2001 |
| JP | 2003-149179 | 5/2003 |
| WO | 03/076699 | 9/2003 |

* cited by examiner

*Primary Examiner*—Courtney Thomas
*Assistant Examiner*—Jurie Yun
(74) *Attorney, Agent, or Firm*—Antonelli, Terry, Stout and Kraus, LLP.

(57) ABSTRACT

An X-ray crystal orientation measuring apparatus and a method thereof, for enabling to measure distribution of crystal orientations upon a crystal having the sub-grain structure, lineage structure, other than the single domain, with using X-ray, comprises, an XY stage 20 for mounting a crystal S to be measured thereon and being movable in X-Y directions, an X-ray generating device 50 for irradiating X-ray at a predetermined angle upon a measuring surface of the crystal to be measured on the stage, a high-sensitive two-dimensional detector 60 for detecting the diffraction image of X-ray, which is irradiated from the X-ray generating device upon the measuring surface of the crystal to be measured, and a control PC, wherein the control PC calculates out a central position of the diffraction image detected, from the detected screen, so as to calculate out the crystal orientation upon the measuring surface of the crystal to be measured.

16 Claims, 6 Drawing Sheets

$K_0$: INCIDENT X-RAY
$K$ : DIFFRACTED X-RAY
$V$ : NORMAL LINE OF DIFFRACTION PLANE

PROJECTION LINE OF
VECTOR V ON X-Y PLANE

Grain i    Grain j

X-RAY CRYSTAL ORIENTATION MEASURING METHOD AND X-RAY CRYSTAL ORIENTATION MEASURING APPARATUS

BACKGROUND OF THE INVENTION

The present invention relates to an X-ray crystal orientation measuring method and an X-ray crystal orientation measuring apparatus, for measuring an orientation of a crystal with using X-ray.

An orientation measurement for a crystal can be applied to a single crystal material. And, such the measurement of the crystal orientation is made for studying on the direction of growth of the crystal axis, in particular, with respect to an outer configuration of the crystal, and in that instance, in general, there are already known a method for determining all of the orientations in three (3) axes and also a planner-orientation measurement for studying a direction of a normal line on a specific lattice plane.

The present invention relates, in particular, to such the planner-orientation measurement, and this planner-orientation measurement is applicable when full three (3) axis orientation is known by or from outer configuration due to habits and/or cleaves of the crystal, and therefore it is applied in a case when trying to cut the crystal, accurately, on a specific surface thereof. A representative one of this is a method, being so-called "Cut Surface Inspection Method", for example.

However, the single crystal mentioned above differs in the mechanical, optical and/or electro-magnetic characteristics, depending upon the crystal orientations thereof (i.e., having an anisotropy). For that reason, in order to utilize such the characteristics of the crystal in positive manner, the single crystal must be studied upon the crystal orientation thereof, in advance, and must be cut out into a desired direction (such as, cutting at a specific orientation), to be used. For that purpose mentioned above, also, the crystal orientation measurement is necessary, to which the present invention relates.

By the way, in the Patent Document 1, which will be mentioned below, there is already known a method and an apparatus thereof, wherein a measurement is made upon an incident angle of X-ray, at which the Bragg reflection occurs, with using a characteristic X-ray, and this operation is conducted in four (4) directions, each separating by 90 degree in the angle, or alternately, two (2) directions, each separating by 180 degree in the angle, upon a surface of the crystal plate, thereby measuring the required planner orientation from the already-known Bragg angles. However, such planner orientation measuring apparatus is already available on markets, as a product of applying such the measurement method therein, such as, by the name of "FSAS" or "SAM", for example.

And, there is also already known a method for measuring the crystal orientation, through measuring an incident angle of the X-ray where the Bragg reflection occurs with using the characteristic X-ray, as well as, studying upon which position the diffracted X-ray is incident, at the same time, in Patent Document 2, which will be mentioned below.

Patent Document 1: Japanese Patent Publication No. Hei 4-59581 (1992) (corresponding JP Laying-Open No. Sho-57-136151 (1982)), and in particular, FIG. 3 thereof; and Patent Document 2: Japanese Patent Publication No. Hei 3-58058 (1991) (corresponding JP Laying-Open No. Sho-57-136150 (1982)), and in particular, FIG. 4 thereof.

However, with such the method relating to the conventional arts mentioned above, it is indispensable to make an operation, i.e., scanning the X-ray at the incident angle (angle ω) thereof within a predetermined region. And, if the crystal is chained in the kind thereof or in the lattice plane index thereof, for example, since the diffraction angle 2θ thereof also changes, therefore it is necessary to set up an optical system for measurement, again, for each time. For this reason, there is a drawback that it is necessary to provide a complex mechanism, such as, a scanning mechanism, thereby bringing the apparatus itself to be expensive in manufacturing. In particular, with the method of the Patent Document 1 mentioned above, since the scanning must be made four (4) times or two (2) times, and since it is necessary to make determination upon upper and lower positions of the diffracted ray, therefore there is a drawback that it takes a time for the measurement. Also, with the method known by the Patent Document 2 mentioned above, after the scanning ω, since it is necessary to study the position on the detector, where the X-ray is incident upon, while returning this angle ω to a peak value to be fixed thereat; therefore, there is also a drawback or problem that it takes a time for the measurement.

Further, with the method of the Patent Document 1 mentioned above, it is assumed that a target of measurement is a single domain; i.e., the crystal, in which atoms or molecules are disposed or arranged, regularly and cyclically, and therefore the crystal orientation is directed always in the same if studying thereof in any position of the crystal. Then, if applying the method to other crystals having the structures, such as: the sub-grain structure <i.e., the crystal, with which it is difficult to obtain such the single domain as was mentioned above, and it is made up with a large number of crystal grains, for example, crystal of fluorite ($CaF_2$), crystal of magnesia (MgO), crystal of ferrite, etc. >; the lineage structure<i.e., it is a kind of defective structure, so that it may show a behavior, depending on the position, that the orientation of the crystal changes continuously. For example, this can be found in sapphire of oxide crystal, LN (Lithium Niobium Oxide: $LiNbO_3$), LT (Lithium Tantalum Oxide: $LiTaO_3$), etc.>, there may occur a case where the X-ray does not irradiated upon the same position on the crystal in the operations of four (4) times or the two (2) times of scanning of the angle ω; therefore, there is a drawback of coming out an erroneous result therefrom.

And, in particular, when measuring a distribution of the orientations on the crystal having such the sub-grain structure and/or the lineage structure, other than the single domain, there is a necessity of so-called a mapping measurement, i.e., for measuring the orientation at plural numbers of measuring points upon the measuring surface thereof. For this reason, with such the methods already known by the above Patent Documents 1 and 2, as is apparent from the method mentioned above, a considerable long time is necessary only for one (1) time of measurement itself (i.e., the measurement at one (1) point), therefore, in particular, in a case when trying to make the measurement of the orientation at a large number of measuring points, through the mapping measurement, there is the drawback of taking an expansively large amount of time.

BRIEF SUMMARY OF THE INVENTION

Then, according to the present invention, for dissolving such the drawbacks in relation to the conventional arts mentioned above, namely, an object thereof is to provide an X-ray crystal orientation measuring apparatus, with which a time necessary for the crystal orientation measurement at one (1) timer (at one (1) point) is short, even when making the measurement of the orientation distribution upon the crystal having the structure other than the single domain, such as, the sub-grain structure or the lineage structure, in other words, upon the crystal which necessitates the mapping measurement, thereby enabling the measurement on distribution of the crystal orientations, but without taking such a long time even when achieving the mapping measurement at a large number of points, and further, an X-ray crystal orientation measuring method being suitable for obtaining such the apparatus as was mentioned above.

For accomplishing such the object as was mentioned above, according to the present invention, first of all, there is provided an X-ray crystal orientation measuring method, comprising the following steps of: irradiating continuous X-rays upon a measuring surface of a crystal to be measured at a predetermined angle; detecting spots obtained through irradiation of said continuous X-rays, corresponding to a lattice plane of the crystal, by means of a two-dimension detector; and measuring a central position of said detected spots, whereby calculating out a normal line of the lattice plane of said crystal upon basis of said central point measured.

And, according to the present invention, in the X-ray crystal orientation measuring method, as described in the above, it is preferable that the measurement in accordance with the measuring method mentioned above is executed at plural numbers of portions upon the measuring surface of the crystal to be measured, whereby measuring a distribution of orientations on the measuring surface of said crystal, or that the spots obtained through irradiation of said continuous X-rays upon the measuring surface of said crystal to be measured are Laue spots.

Also, according to the present invention, for accomplishing the object mentioned above, there is further provided an X-ray crystal orientation measuring apparatus, for measuring a crystal orientation upon a measuring surface of a crystal to be measured, with using X-ray, comprising: a sample mounting means for mounting a crystal to be measured thereon, being movable in a horizontal direction; means for irradiating X-ray at a predetermined angle upon the measuring surface of said crystal to be measured, which is mounted on said sample mounting means; means for detecting a diffraction image of the X-ray irradiated from said X-ray irradiating means upon the measuring surface of said crystal to be measured; and means for calculating out the crystal orientation upon the measuring surface of said crystal to be measured, from the diffraction image detected by said detection means.

Further, according to the present invention, in the X-ray crystal orientation measuring apparatus, as mentioned in the above, it is preferable that said calculating means calculates out a center point of the diffraction image detected by said detection means, whereby calculating out the crystal orientation upon the measuring surface of said crystal to be measured, that the spots detected by said detection means are Laue spots. In addition thereto, it is also preferable that said detection means is movable in a part thereof, whereby bringing a camera length thereof to be adjustable, that said X-ray irradiation means and said detection means are attached, so that an irradiation direction of the X-ray and an incident direction thereof are equal to each other with respect to the measuring surface of said crystal to be measured, and that said X-ray irradiation means and said detection means are movable in direction of a normal line to the measuring surface of said crystal to be measured, which is mounted on said sample mounting means.

BRIEF DESCRIPTION OF THE SEVERAL VIEWS OF THE DRAWING

Those and other objects, features and advantages of the present invention will become more readily apparent from the following detailed description when taken in conjunction with the accompanying drawings wherein.

DETAILED DESCRIPTION OF THE INVENTION

Hereinafter, embodiments according to the present invention will be fully explained by referring to the attached drawings.

However, hereinafter, an X-ray crystal orientation measuring apparatus according to the present embodiment is an apparatus for measuring the orientation distribution about a crystal of the sub-grain structure (for example, a crystal of fluorite), in particular, of which it is difficult to obtain the single domain crystal.

Figure 1:
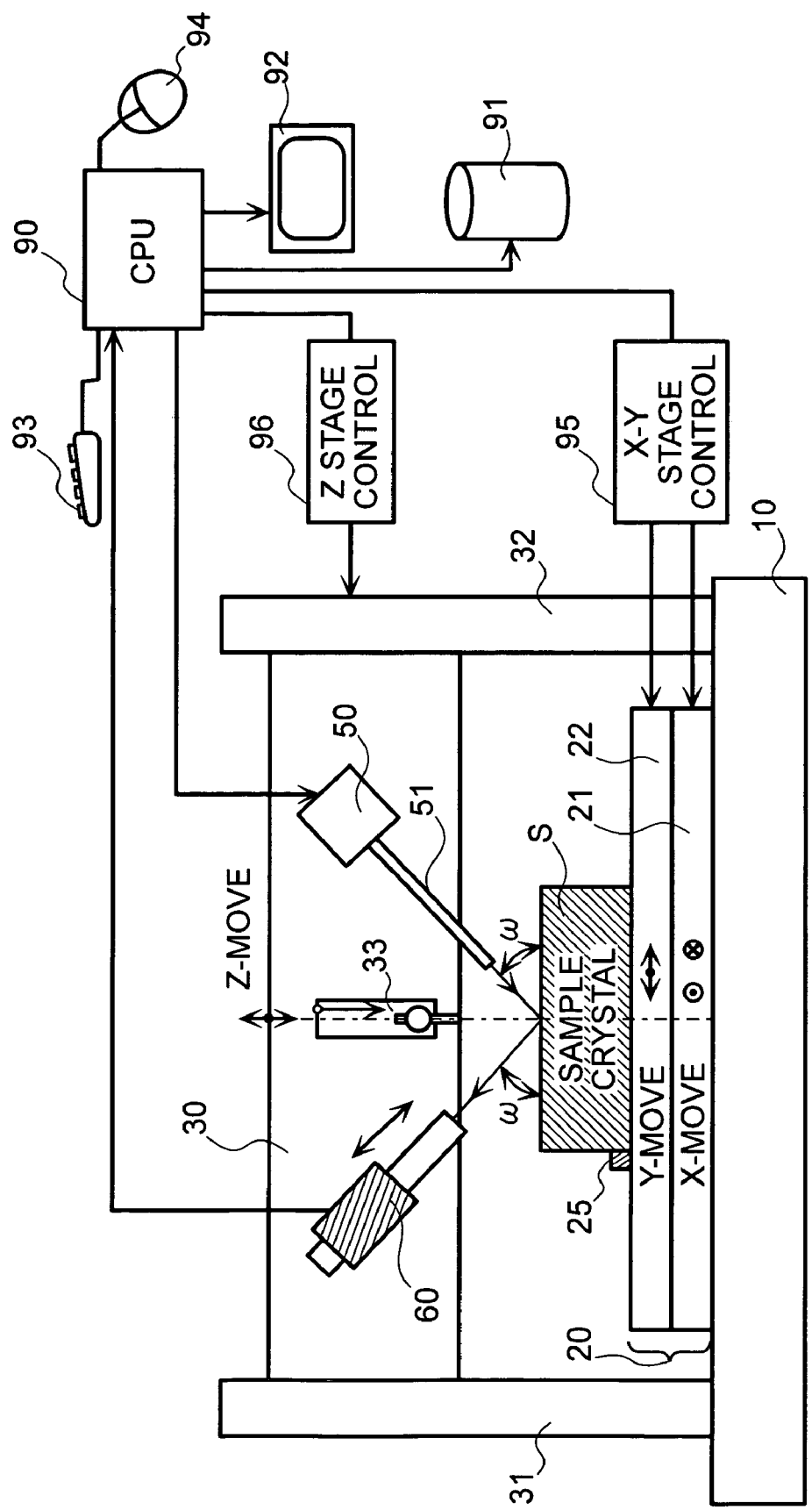
FIG. 1 is a view for showing a brief structure of an X-ray crystal orientation measuring apparatus, according to one embodiment of the present invention.

Firstly, FIG. 1 attached herewith shows the structure of a main portion of the X-ray crystal orientation measuring apparatus according to the present embodiment.

Namely, in this FIG. 1, a reference numeral 10 depicts a basement of the apparatus, and on this basement 10 is disposed so-called an XY stage 20, being made up with movable X table 21 and Y table 22, for mounting a sample S thereon and crossing at right angles with each other. Also, on the basement 10 is disposed a wall 30 for mounting an optic system thereon, which is formed to be gate-like in the outer shape thereof, with fixing the support legs 31 and 32 thereon, thereby bridging over the XY stage 20 mentioned above. Further, this optic system-fixing wall 30 is also movable in direction of an arrow (i.e., up and down: Z move) in the figure, by means of a driving apparatus, such as, a pulse motor, etc., for example, in the similar manner to that of the X table 21 and the Y table 22 of the XY stage 20 mentioned above. Moreover, a reference numeral 33 in the figure depicts a gauge for Z position correcting, for correcting the Z position of the optic system-fixing wall 30. Also, a reference numeral 25 in the figure depicts a guide for positioning the sample, which is attached on the Y table 22 of the XY stage 20, but the details of which will be mentioned later. Further, the entire of those is covered with an anti-X-ray (or X-ray proof) cover not shown in the figure.

And, as apparent from the FIG. 1, in the X-ray crystal orientation measuring apparatus mentioned above, a measurement optic system thereof is built up with an X-ray generating device 50, being an X-ray source, a collimator 51 for bringing the X-rays generated therefrom (so-called, continuous X-rays) into parallel X-rays, and a high-sensitive two(2)-dimensional detector (or a X-ray high-sensitive TV) 60, which is built up with, such as, a COD of two (2) dimensions (plate-like), for example. However, an angle of the collimator 51 is set up, so that the X-ray is incident upon the measuring surface of the sample S on the XY stage 20, at a predetermined angle ω (for example, ω=60 degree). Also, this collimator is a double-pinhole collimator having, such as, a hole of 0.3 mmφ to 0.5 mmφ, for example. Also, an exist distance between X-ray source and the collimator is about 200 to 250 mm, and the distance up to the sample S is about 300 mm. The X-ray source and the collimator are fixed. If making the camera length long, an improvement can be obtained on accuracy of measuring the orientation, however when a large shift occurs in the orientation, it comes out from the detection surface; therefore, it is impossible to measure it. On the other hand, if making the camera length short, it is possible to deal with such the large shift in the orientation. For this reason, the camera length is set up, appropriately, depending upon the condition of the sample crystal.

On the other hand, the high-sensitive two-dimensional detector 60 is disposed in a manner, so that it can catch the diffraction image (i.e., the Laue image), which is obtained from diffraction of the X-ray, which is emitted from the collimator 51 mentioned above, upon the measuring surface of the sample S; i.e., a normal line perpendicular to that measuring surface also defines the equal angle ω to the measuring surface on the sample S. Further, this high-sensitive two-dimensional detector 60 is movable, freely in direction of an arrow in the figure, by means of the driving apparatus, such as, the pulse motor, etc., too. Thus, with such the structure, the camera length "L" (see FIG. 9) is variable (i.e., slidable), and the variable region or range thereof is, for example, nearly from 100 to 300 mm. However, in such the structure mentioned above, the X-ray source and the collimator must be fixed on the optic system-fixing wall 30 while keeping a predetermined relationship between them. An electric power source of the X-ray generating device 50 can be disposed in an outside thereof.

Also, a reference numeral 90 in the figure depicts a control PC (CPU), and it comprises a memory device, such as, a hard disk drive, etc., in a part thereof, wherein various kinds of software are stored in the said memory device, for executing a control and/or a measurement for an each portion of the apparatus, or alternately, there can be stored the pictures and/or the measuring results obtained, in a part thereof. Also, this control PC 90 comprises a display device 92, for presenting thereon the diffraction image (i.e., the Laue image) obtained through the high-sensitive two-dimensional detector 60 to an operator, further an input device, including a keyboard 93 and/or a mouse 94. etc., for example, and an output device, such as, a printer, etc., though not shown in the figure. In addition thereto, the control PC 90 controls the positions of the X table 21 and the Y table 22 of the XY stage 20, as well as, the position of the Z stage, through the X-Y stage control device 95 and the Z stage control device 96, and further, it controls the camera length of the high-sensitive two-dimensional detector 60.

Figure 2:
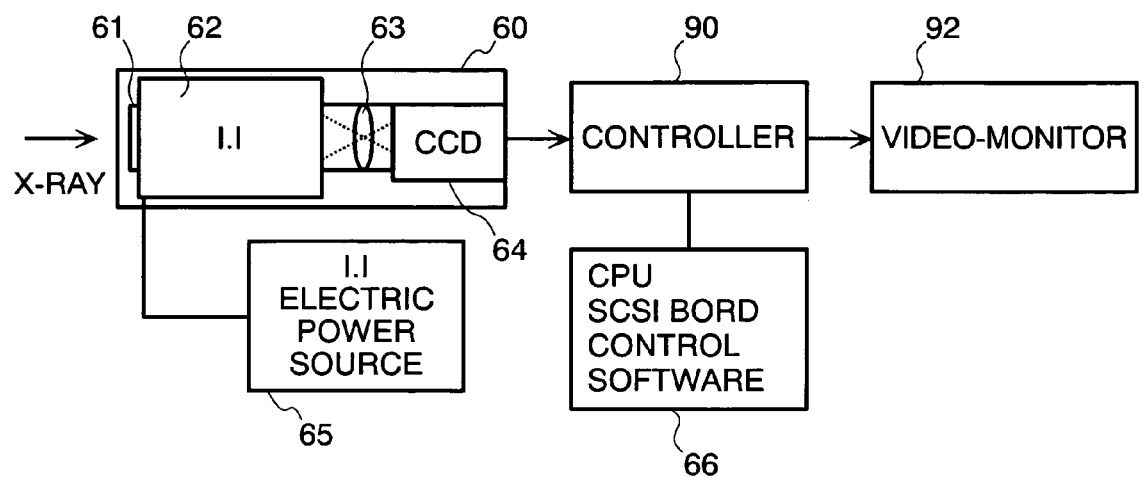
FIG. 2 is a cross-section view for showing the details of a high-sensitive two-dimension detector in the X-ray crystal orientation measuring apparatus, according to one embodiment of the present invention.

Next, in FIG. 2 attached herewith, there is shown an example of the detailed structure of the high-sensitive two-dimensional detector 60 mentioned above. Namely, within this detector 60, on a side, upon which the X-ray is incident, there are provided a scintillator 61 for generating a light due to the incident X-ray thereupon, and an I.I (an image intensifier) 62 for amplifying or intensifying the diffraction image (i.e., the Laue image) obtained upon the scintillator, and further, wherein the light amplified within this I.I is incident upon the CCD device 64 of two (2) dimension (in a surface-like form; for example, about 20 mm×20 mm), by the function of a coupling lens 63 disposed behind it, thereby forming an image, to be converted into an electric signal thereof. However, in this FIG. 2, a reference numeral 65 depicts an electric power source of the I.I mentioned above, and the controller is built up with the control PC (i.e., the CPU) 90 shown in FIG. 1 mentioned above. And, this controller takes in an image, which is formed on the CCD, with using the control software that is stored within the memory device 91 shown in FIG. 1, for example, as well as, using a take-in board 66 for a CPU image, and at the same time, it displays the image that is taken into, upon the video monitor 92 thereof (i.e., the display device shown in FIG. 1).

Hereinafter, explanation will be given, in details thereof, about the principle for measuring the orientation distribution on a crystal, with using the X-ray crystal orientation measuring apparatus, the structure of which was already given in hereinbefore, as well as, a method thereof.

1. Measuring Principle 1.1 Measurement

Figure 3:
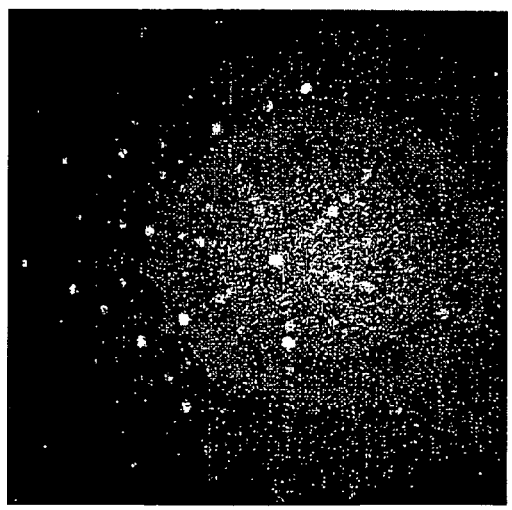
FIG. 3 is a view for showing an example of the diffraction image (i.e., the Laue image), for explaining the principle for measuring the crystal orientation, in the X-ray crystal orientation measuring apparatus according to one embodiment of the present invention.

A measuring principle adopted by the present apparatus lies in the Laue method. However, as a crystal to be dealt with it, it is a crystal, which is cut upon a planner orientation, about (111), and other than that, the present apparatus can deal with the cases of those of (100) and (110). Upon those main indexes, the Laue spots are strong in the intensity (i.e., a white portion on the photo), but spaces around that are opened in the condition (i.e., black portion on the photo). This condition can be observed on a wide-area Laue image, which can be obtained by setting the distance between the sample and the two-dimensional detector (it is called by the "camera length") to be short. This wide-area Laue image is shown in FIG. 3 attached herewith. The spot at the center of the figure corresponds to (111), and around it is opened. According to the present invention, in particular, attention is paid only the position of that spot at (111) in this. Namely, taking the camera length to be long enables a clear observation on the position of only (111), as is shown by 100 in FIG. 4 attached herewith. With measuring that position accurately, the crystal orientation measurement is conducted.

The principle of measurement mentioned above will be shown in FIG. 5 attached herewith. In (xyz) rectangular coordinates system in the figure, the sample surface, on which the orientation is measured, is disposed, to be coincident with the x,y plane thereof. On the other hand, the incident X-ray lies within the y,z plane, being incident upon at the angle o with respect to the sample surface, and it irradiates at the origin of the coordinates. This incident X-ray is diffracted on a lattice plane (111), being nearly parallel with the sample surface (further, in the similar manner, in the cases when it is (100) and (110)). As a result of this, the diffraction image (i.e., the Laue image) can be caught on the TV camera, being the two-dimensional detector, which is disposed in direction of an emission at the angle ω, too, on the y,z plane of the coordinates.

Figure 5:
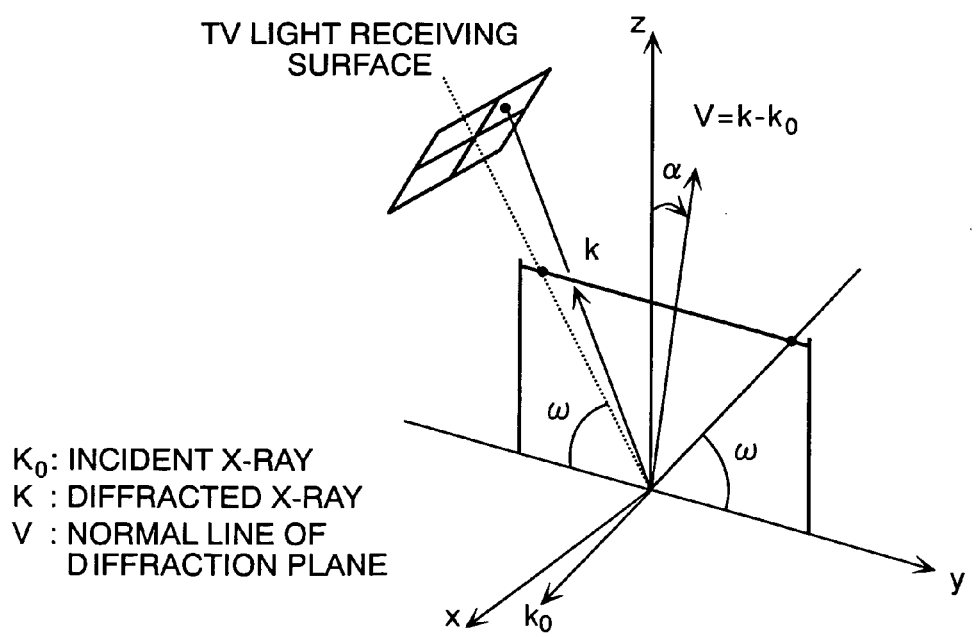
FIG. 5 is an explanatory view for explaining the principle for measuring the crystal orientation, in particular, about a normal line vector of the lattice plane, in the X-ray crystal orientation measuring apparatus mentioned above.

Further, in this FIG. 5, "$k_0$" is a vector indicative of the incident X-ray, and "k" a vector indicative of the direction of the diffracted rays. This vector "k" indicative of the direction of the diffracted rays can be obtained from the position of the diffracted image on the light-receiving surface of the TV mentioned above; i.e., it can be calculated out from vector calculation, which will be mentioned below, as a normal line vector "V" perpendicular to the lattice plane.

Figure 4:
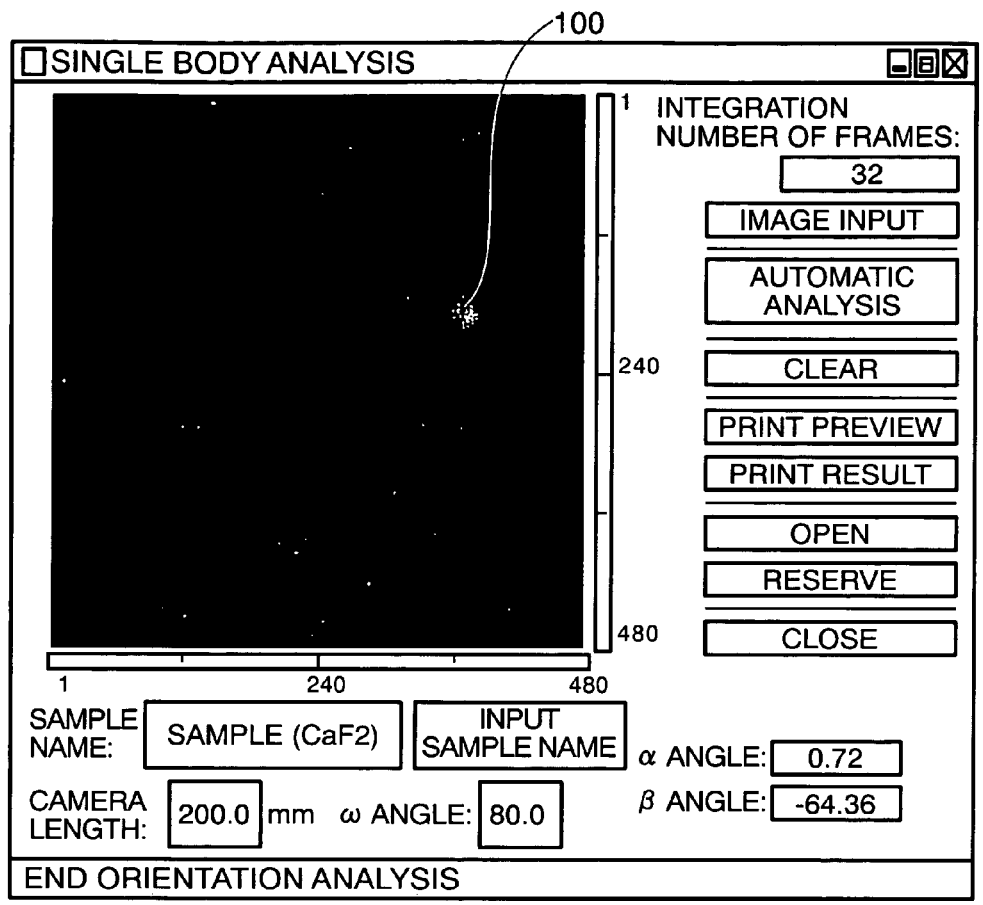
FIG. 4 is a view for showing an example of an observation image of a central point (i.e., the center of gravity of spots) of the diffraction image (i.e., the Laue image), for explaining the principle for measuring the crystal orientation, in the X-ray crystal orientation measuring apparatus mentioned above.

Namely, the spot 100 in FIG. 4 mentioned above is the diffraction image on the fluorite (111), which is caught on the TV camera of the present apparatus, and from this diffraction image, the centroidal positions of the spots can be measured through an automatic pear-search (for example, digitalizing processing of an image), and therefore, it is possible to calculate out the planner orientation thereof, as will be explained below.

1.2 Expression of the Planner Orientation

Figure 6:
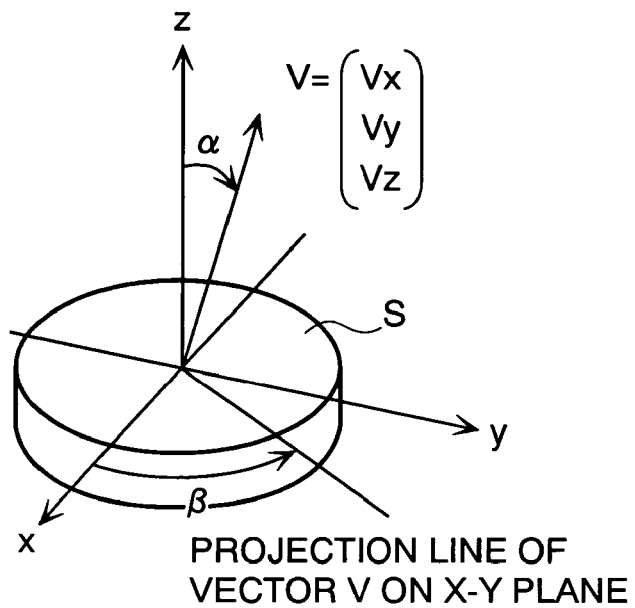
FIG. 6 is also an explanatory view for explaining the principle for measuring the crystal orientation, in particular, about an inclination angel $\alpha$ of the lattice plane and a direction of the inclination $\beta$, in the X-ray crystal orientation measuring apparatus mentioned above.

By referring to FIG. 6 attached herewith, after converting the normal vector "V" of lattice plane into unit vectors, the planner orientation can be presented by by Vx, Vy and Vz, the components thereof, and orientation angles "α" and "β" shown in the figure. Herein, the angle "α" indicates an angle, being defined between the normal lie of the sample surface (i.e., the z axis) and the normal line of the lattice plane, while the angle "β" an angle, being defined between a projection line of the normal line of the lattice plane onto the x,y plane (i.e., the sample surface) and the x axis, and further those angels "α" and "β" can be calculated out through the following equations:

$$\alpha = \cos^{-1} V_z \quad \text{(Eq. 1)}$$

$$\beta = \cos^{-1}(V_x/\text{sqrt}(V_x^2 + V_y^2)) \quad \text{(Eq. 2)}$$

Where, the "sqrt" in the equation mentioned above indicates a square root.

Figure 7:
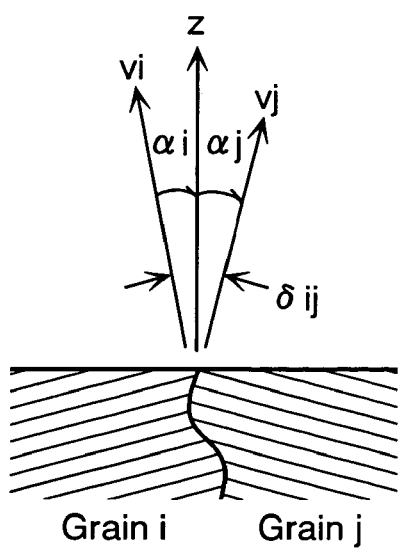
FIG. 7 is a view for explaining about an angle defined by the normal line of the lattice plane, between two (2) crystal grains on a crystal having sub-grain structure.

Also, as is shown in FIG. 7 attached herewith, in particular, there is also outputted an angle "δij", which is defined by the normal lines of lattice planes between the crystal grains in the crystal of grain structure, as a value indicative of scatter or dispersion on the orientation. This "δij" can be calculated out by the following equation:

$$\delta ij = \cos^{-1} Vi \cdot Vj = \cos^{-1}(VixVjx + ViyVjy + VizVjz) \quad \text{(Eq. 3)}$$

However, the "Vi" and "Vj" represent the normal line vectors of lattice plane on grain "i" and grain "j", respectively. And, the components of those are indicted by "Vix", "Viy" and "Viz", and "Vjx", "Vjy" and "Vjz".

1.3 Calculation of the Vector "V"

Figure 8:
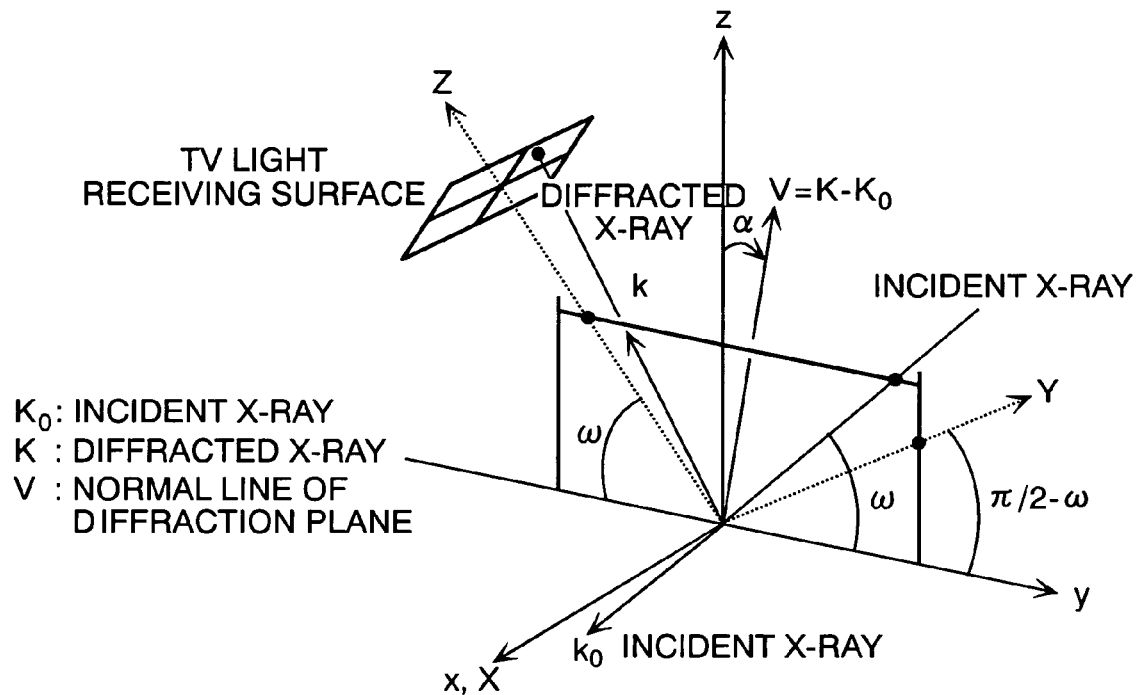
FIG. 8 is a view for explaining a way of obtaining the normal line vector on the lattice plane mentioned above.

The lattice-plane normal vector "V" mentioned above, it can be obtained by the following processes:

First, assuming that the incident X-ray vector "$k_0$" is at "ω" in the incident angle thereof, in FIG. 8 attached herewith, then it can be expressed as follows, in the rectangular coordinates system (xyz):

$$k_0 = \begin{pmatrix} 0 \\ -\cos\omega \\ -\sin\omega \end{pmatrix} \quad \text{(Eq. 4)}$$

Figure 9:
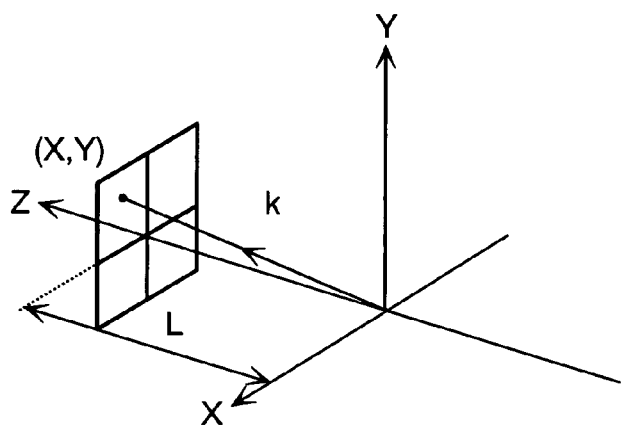
FIG. 9 is a view for showing the vector in the direction of diffracted X-ray mentioned above, but within a (XYZ) system.

Next, as shown in FIG. 9 attached herewith, assuming that the camera length is "L" and the coordinates of the Laue image is (X,Y) on the detector surface, then the diffracted X-ray direction vector "k" can be given by the following, in the rectangular coordinates system (XYZ).

$$k = \begin{pmatrix} X \\ Y \\ L \end{pmatrix} / \text{sqrt}(X^2 + Y^2 + L^2) \equiv \begin{pmatrix} kx \\ ky \\ kz \end{pmatrix} \quad \text{(Eq. 5)}$$

Further, if presenting the diffracted X-ray direction vector "k" mentioned above in the (xyz) system, it can be given by the following equation:

$$k = \begin{pmatrix} 1 & 0 & 0 \\ 0 & \sin\omega & -\cos\omega \\ 0 & \cos\omega & \sin\omega \end{pmatrix} \cdot \begin{pmatrix} kx \\ ky \\ kz \end{pmatrix} = \begin{pmatrix} kx \\ ky\sin\omega - kz\cos\omega \\ kz\cos\omega + kz\sin\omega \end{pmatrix} \quad \text{(Eq. 6)}$$

From the above, the lattice plane normal vector can be calculated out by the following equation.

$$V = (k - k_0)/|k - k_0| \quad \text{(Eq. 7)}$$

2. Measuring Steps 2.1 Mounting of Sample

Figure 10:
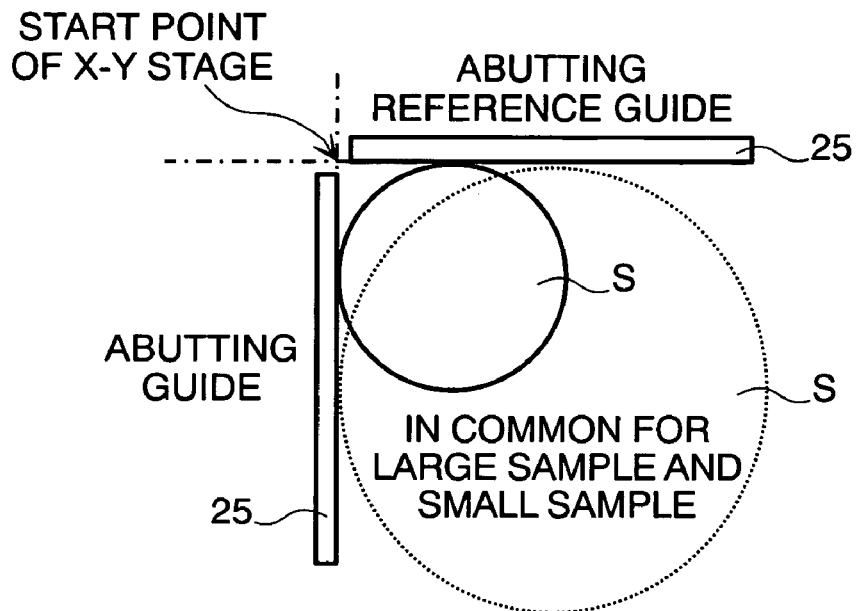
FIG. 10 is a view for showing a method for mounting a sample on the X-ray crystal orientation measuring apparatus mentioned above.

First, a crystal (i.e., the crystal to be measured) S, being the sample, on which the measurement is made upon the orientation distribution on the surface thereof, is disposed on the XY stage 20 of the X-ray crystal orientation measuring apparatus. As was shown in FIG. 6 mentioned above, in general, this sample crystal S has the outer configuration, being about cylinder-like or disk-like, and therefore, as is also shown in FIG. 10 attached herewith, it is positioned by abutting a side surface thereof onto the so-called abutting reference guides 25 and 25, which are provided along the X axis and the Y axis, extending perpendicular to each other into direction of the origin on the XY stage 20 mentioned above. However, the sample has the size, in the case of the fluorite mentioned above, of about 400 mmφ (100 mm in thickness), for a larger one, to be measured, or for a small one, can be assumed so-called the wafer-like, but the minimum value thereof is about 10 mmφ (0.5 mm in thickness). However, in any case of those, with using the abutting reference guides 25 and 25 mentioned above, it is possible to position the sample, at the optimal position thereof, irrespective of the sizes (i.e., being large or small) of the sample, in common.

2.2 Mapping Measurement

Following to the above, for conducting the mapping measurement with shifting or moving the XY stage 20, determination is made on a stroke, as well as, a mesh size, in direction of the X axis and Y axis, depending upon the sample size mentioned above, while taking the diameter of the sample to be measured or the like into the consideration thereof. For example, the stroke for moving is set about 410 mm, for a large sample, and the resolving power thereof is about 0.02 mm. The mesh size is set at from a several mm up to several tens mm. Further, the determination on those stroke and the mesh size can be made by inputting data necessary for them into the control PC 90, through the keyboard 93 or the like of the input device mentioned above. Also, in this instance, it is preferable to input the diameter of that crystal, and in addition thereto, the position is also moved in the Z-axis direction, to be adjusted, for the measurement optic system, which is fixedly disposed on the optic system-fixing wall 30, depending upon the size of the sample, in particular, the thickness thereof.

Figure 11A:
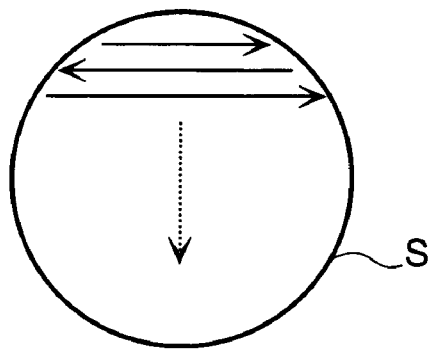
FIGS. 11(A) and 11(B) are views for explaining a mapping measurement, with the X-ray crystal orientation measuring apparatus mentioned above.
Figure 11B:
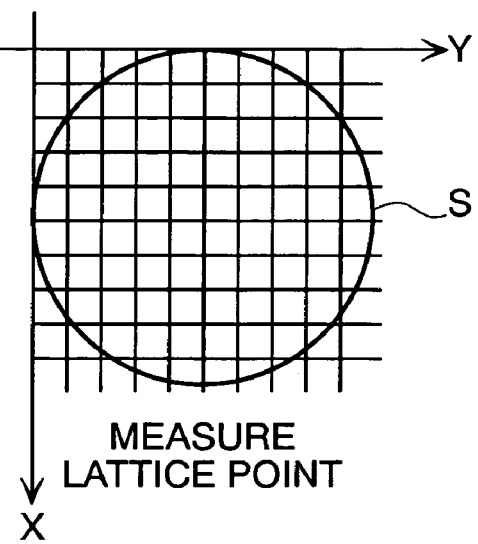

Next, the apparatus mentioned above is operated, so as to execute the measurement of the orientation distribution upon the sample surface. Namely, as shown in FIG. 10, while moving the XY stage 20 mentioned above along with the X-axis and the Y-axis thereof, sequentially, following the stroke set up in the above (see FIG. 11(*a*)), the measurement is made on the lattice orientation at each point of measurement. Thereafter, a result of measurement is displayed in the following manner.

2.3 Display of Measurement Result

After measurement mentioned above, the results of the measurement are displayed on the display device 92. In that instance, it is possible to edit the measurement values of the crystal orientations obtained in the expressions, such as, a table of numerical values, a display of histogram, a display of a map, a display of distribution, etc., for example, by means of the CPU 90 mentioned above.

In this manner, with the X-ray crystal orientation measuring apparatus and also the crystal orientation measuring method in such the apparatus mentioned above, according to the embodiment of the present invention, the Laue method and the two-dimensional detector are applied therein, and as a result thereof, even if changing the crystal in the kind thereof and/or the lattice plane index thereof; such as, the planner orientation is changed into (100), (110) and (111), for example, however, it is possible to study the lattice plane (i.e., the diffraction surface) through the same optic system. In that instance, since there is no necessity at all of moving the scan or the like for the orientation measurement, therefore the optic system for measurement is enough to stay fixing at (thus, there is no necessity of moving the optic system). In more details, it is achieved by means of the high-sensitive two-dimensional detector based on the CCD, wherein the Laue spots is detected corresponding to the lattice plane, and the direction of the lattice plane normal line is calculated out at that position (i.e., determining the surface direction).

And, for obtaining the distribution of the crystal orientations upon the sample surface, while moving the XY stage 20 mentioned above, an image or picture is taken into, at an each measuring point, which can be obtained through the high-sensitive two-dimension detector 60 for an integration time of about one (1) second. However, this integration can be achieved through, such as, the CCD on-chip integration. Thereafter, for the image taken into, the centroid thereof can be obtained through an automatic peak search, and further, the planner orientation can be calculated out according to the calculation equation mentioned above. Thus, repetition of such the measurement as was mentioned over the entire region of measurement, which is set up on the sample surface, enables the measurement of the crystal orientations at the respective portions thereof, in the form of a mesh-like map (see FIG. 11(*b*)).

Further, in addition to the automatic measurement mentioned above, it is also possible to conduct so-called a real-time observation; i.e., while conducting X step movement and Y step movement, an eye or visual observation can be made upon the diffraction image displayed on the video monitor, through operations of stopping and/or returning in position with using a mouse operation therein. Namely, if there is a shift in the crystal orientation upon the sample surface, the observed diffraction image moves on the monitor.

Further, from a result of measurement that was actually conducted upon the crystal orientation of the sample, with using the apparatus mentioned above, it is possible to make measurement of the planner orientation, for each one (1) point, in a short time, i.e., about 2–3 seconds, including the time for movement on the X and Y axes therein. With this, it is possible to achieve shortening of a unit time for the crystal orientation measurement (i.e., the orientation measuring for one (1) measurement point). For this reason, it does not take much time, in particular if conducting the mapping measurement, wherein measurement is made at a large numbers of points, thereby obtaining the X-ray crystal orientation measuring apparatus being practically suitable.

The present invention may be embodied in other specific forms without departing from the spirit or essential feature or characteristics thereof. The present embodiment(s) is/are therefore to be considered in all respects as illustrative and not restrictive, the scope of the invention being indicated by the appended claims rather than by the forgoing description and range of equivalency of the claims are therefore to be embraces therein.

What is claimed is:

1. An X-ray crystal orientation measuring method, comprising:
   irradiating X-rays upon a measuring surface of a crystal to be measured, at a predetermined angle;
   detecting a diffraction pattern corresponding to a lattice plane of the crystal obtained through irradiation of said X-rays, by means of a two-dimension detector; and
   measuring a central position exclusively of a central spot of said diffraction pattern, and
   calculating a normal line of a lattice plane of said crystal on a basis of said position of said central spot for determining a crystal orientation of a measuring surface of said crystal.

2. The X-ray crystal orientation measuring method, as claimed in claim 1, wherein the measuring is executed at plural locations on the measuring surface of the crystal to be measured, thereby measuring a distribution of crystal orientations on the measuring surface of said crystal.

3. The X-ray crystal orientation measuring method, as claimed in claim 1, wherein the central spots obtained through the irradiating of said X-rays upon the measuring surface of said crystal to be measured, are Laue spots.

4. The X-ray crystal orientation measuring method, as claimed in claim 1, wherein the irradiating irradiates continuous X-rays upon the measuring surface of the crystal to be measured.

5. An X-ray crystal orientation measuring apparatus for detecting a crystal orientation on a measuring surface of a crystal to be measured using X-ray radiation, comprising:
   a sample mounting means for mounting a crystal to be measured thereon, and being movable in a horizontal direction;

means for irradiating X-ray radiation at a predetermined angle upon the measuring surface of said crystal to be measured, where said crystal is mounted on said sample mounting means;

means for detecting a diffraction pattern of the X-ray radiation irradiated from said irradiating means upon the measuring surface of said crystal using a two-dimensional detector; and means for calculating the crystal orientation of the measuring surface of said crystal from said diffraction pattern, wherein the crystal orientation is determined from a central position of exclusively a central one of the spots of the diffraction pattern detected by said detection means.

6. The X-ray crystal orientation measuring apparatus, as claimed in claim 5, wherein the spots detected by said detecting means, are Laue spots.

7. The X-ray crystal orientation measuring apparatus, as claimed in claim 5, wherein said detecting means is at least partially movable to allow a camera length thereof to be adjustable.

8. The X-ray crystal orientation measuring apparatus, as claimed in claim 5, wherein said irradiating means and said detecting means are arranged, so that an irradiation angle of the X-ray radiation and a detection angle of the X-ray radiation are equal to each other with respect to the measuring surface of said crystal to be measured.

9. The X-ray crystal orientation measuring apparatus, as claimed in claim 5, wherein said irradiating means and said detecting means are movable in a direction of a normal line to the measuring surface of said crystal to be measured.

10. The X-ray crystal orientation measuring apparatus, as claimed in claim 5, wherein the irradiating means irradiates continuous X-ray radiation upon the measuring surface of the crystal to be measured.

11. An X-ray crystal orientation measuring apparatus for detecting a crystal orientation on a measuring surface of a crystal to be measured using X-ray radiation, comprising:

a sample mounting table to mount a crystal to be measured thereon, and being movable in a horizontal direction;

an X-ray generator to irradiate X-ray radiation at a predetermined angle upon the measuring surface of said crystal to be measured;

a detector unit to detect a diffraction pattern of the X-ray radiation irradiated from said X-ray generator upon the measuring surface of said crystal using a two-dimensional detector; and a calculating unit to calculate the crystal orientation of the measuring surface of said crystal from said diffraction pattern, wherein the crystal orientation is determined from a central position of exclusively a central one of the spots of the diffraction pattern detected by said detector unit.

12. The X-ray crystal orientation measuring apparatus, as claimed in claim 11, wherein the spots detected by said detector unit, are Laue spots.

13. The X-ray crystal orientation measuring apparatus, as claimed in claim 11, wherein said detector unit is at least partially movable to allow a camera length thereof to be adjustable.

14. The X-ray crystal orientation measuring apparatus, as claimed in claim 11, wherein said X-ray generator and said detector unit are arranged, so that an irradiation angle of the X-ray radiation and a detection angle of the X-ray radiation are equal to each other with respect to the measuring surface of said crystal to be measured.

15. The X-ray crystal orientation measuring apparatus, as claimed in claim 11, wherein said X-ray generator and said detector unit are movable in a direction of a normal line to the measuring surface of said crystal to be measured.

16. The X-ray crystal orientation measuring apparatus, as claimed in claim 11, wherein the X-ray generator is adapted to selectably irradiate continuous X-ray radiation upon the measuring surface of the crystal to be measured.

* * * * *